Figure 1:
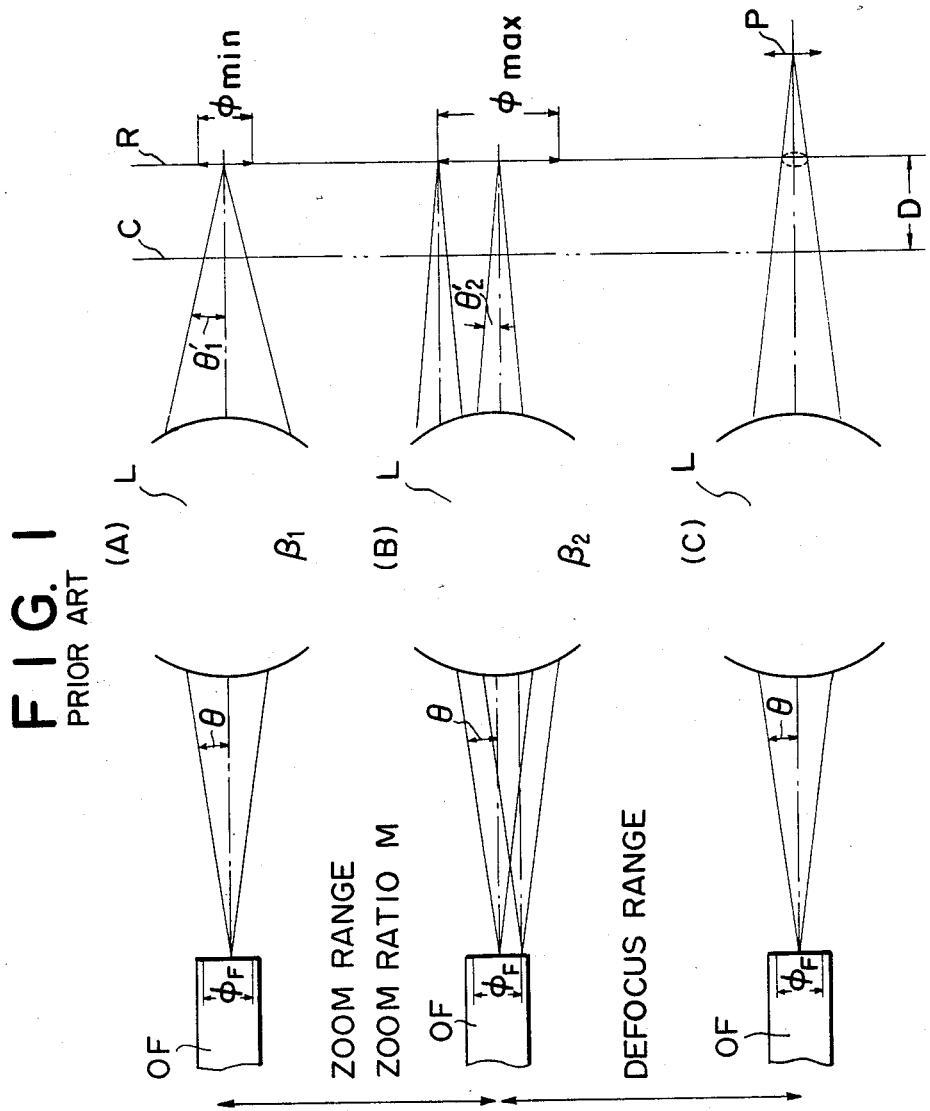

350-96.25
3/18/86   XR   4,576,160   SR

United States Patent [19]
Tanaka

[11] Patent Number: 4,576,160

[45] Date of Patent: Mar. 18, 1986

[54] PHOTOTHERAPEUTIC APPARATUS WITH SPOT SIZE REGULATING MEANS

[75] Inventor: Shinya Tanaka, Tokyo, Japan

[73] Assignee: Tokyo Kogaku Kikai Kabushiki Kaisha, Tokyo, Japan

[21] Appl. No.: 511,330

[22] Filed: Jul. 6, 1983

[30] Foreign Application Priority Data

Jul. 15, 1982 [JP] Japan .................... 57-123398

[51] Int. Cl.$^4$ .............................................. A61B 1/06
[52] U.S. Cl. .................... 128/303.1; 362/32; 350/96.25; 350/254
[58] Field of Search ............ 128/303.1, 395–398; 350/254, 96.24, 96.25, 96.26, 96.27, 6.8; 362/32

[56] References Cited

U.S. PATENT DOCUMENTS

| | | | |
|---|---|---|---|
| 3,554,721 | 1/1971 | Gardner | 350/96.25 |
| 3,580,082 | 5/1971 | Strack | 350/96.24 |
| 3,631,775 | 6/1972 | Tidd | 350/254 |
| 3,925,727 | 12/1975 | Dugway | 350/96.24 |
| 4,353,617 | 10/1982 | Tokumitsu et al. | 350/6.8 |
| 4,398,790 | 8/1983 | Righini et al. | 350/96.1 |
| 4,409,979 | 10/1983 | Roussel et al. | 128/303.1 |

*Primary Examiner*—Edward M. Coven
*Assistant Examiner*—Max F. Hindenburg
*Attorney, Agent, or Firm*—Brumbaugh, Graves, Donohue & Raymond

[57] ABSTRACT

A phototherapeutic apparatus in which a light beam is projected from a therapeutic light source on the therapeutic region of a patient by a spot size regulator in which selection can be made from a plurality of illuminating fiber optic elements of different diameters for coarse regulation and optical magnification can be varied for fine regulation.

7 Claims, 3 Drawing Figures

PHOTOTHERAPEUTIC APPARATUS WITH SPOT SIZE REGULATING MEANS

The present invention relates to a phototherapeutic apparatus such as a laser knife, a laser coagulator and the like.

Although the present invention will be described by way of example in connection with a laser coagulator used in ophthalmology, the present invention is not limited to such an apparatus and can be utilized over a great range of phototherapeutic apparatuses such as xenon light-type coagulators, laser knives and others.

The prior art coagulator includes an argon laser used as a source of light. Light beams from the light source are projected on the therapeutic region of a patient's eye, for example, on the retina or iris, through a condenser lens, an optical fiber, a projecting optical system, a movable mirror for light scan, and a contact lens which is mounted on the patient's eye for eliminating the refractive index of the cornea. On the other hand, the therapeutic region and surrounding areas are illuminated by a source of observing light through an illuminating optical system, so that they can be observed by an operator through an observing optical system. In such an arrangement, the coagulating area (hereinafter called "spot size") of the coagulator is regulated by the use of the above illuminating optical system. For this purpose, there have been realized various types of systems including a system in which a region of the spot size is regulated by the use of a zoom lens while the other region is adjusted by utilizing a defocusing effect, and an illuminating optical system of turret and variable power type.

There can be listed the following four characteristics which are desirable in a spot-size regulating mechanism for the illuminating optical system of the coagulator apparatus:

(i) Diameter of the illumination light beams passed across the cornea should at all times be larger than the spot size with a minimum of about one millimeter. At maximum, it must be of such a magnitude that the light beams cannot be in contact with the iris even at all the conditions of application, such as a condition in which the light beams are obliquely projected.

(ii) Density of energy must become maximum in the therapeutic region. For example, if the retina is to be coagulated, the projected light beams must provide a maximum energy density at the retina in comparison with those at the iris, crystalline lens, vitreous body through all of which the light beams passes, as well as the choroid coat, sclera and others which are located rearwardly of the retina.

(iii) The spot size should be regulated within the range of $50\mu$–$1000\mu$ or more and able to be adjusted in a continuous fashion. If the spot size cannot be regulated in a continuous manner, it must be able to be stepwise adjusted without any significant problem for therapeutic operation.

(iv) The therapeutic apparatus must be sufficiently compact so as not to obstruct an operator on therapy and observation.

Two of the above characteristics (i) and (ii) are required in the viewpoint of safety for patients. The remaining characteristics (iii) and (iv) are required in the standpoint of therapeutic operation.

The prior art spot size regulating mechanism of such a zoom-defocus type as described hereinbefore can fulfill only the characteristics (i) and (iii).

FIG. 1 is an optical diagram showing the principle of the zoom-defocus type spot size regulating mechanism which has bee aforementioned as the prior art. There is a zoom section from FIG. 1(A) to FIG. 1((B). Assume that light beams emitted from the end of a fiber OF are imaged on a therapeutic region, for example, the retina R through an imaging optical system L. FIG. 1(A) shows the imaging optical system L when its magnification is $\beta_1$ while FIG. 1(B) shows the same when the magnification is $\beta_2$. When the light beams are incident on the imaging optical system L with an incident angle $\theta$, the emitting angle $\theta'$ thereof will change to provide $\theta_1'/\theta_2' = M$ in the zoom section where M is the zoom ratio of the imaging optical system. The diameter of the light beams passing through the cornea C is function of the zoom ratio M.

If it is desired that the above spot size regulating mechanism of the prior art can fulfill the above characteristic (ii), the end of the fiber having its core diameter $\phi F$ should be imaged on the retina R with a diameter $\phi$. The following condition must further be fulfilled:

$$\left.\begin{array}{c} 2|F \cdot \tan\theta| < |\phi| \\ \phi = |\beta \phi F| \end{array}\right\} \quad (1)$$

where F is the focal length of the imaging optical system L and $\theta$ is a maximum incident angle of the projecting light beams relative to the imaging optical system L.

Now, assume that there is an optical arrangement in which principal rays becomes parallel to each other at the emitting side when $\phi$ is maximum as shown in FIG. 1(B), for example. Diameter $\phi_c|\phi_{max}$ of light beams passing across the cornea is:

$$\phi_c|\phi_{max} = \phi_{max} + 2D \cdot \tan\theta_2'(\theta_2' = \theta'|\phi_{max})$$

where D is the focal length of the lens of the human's eye (it may be an optical path from the cornea C to the retina R).

When $\phi$ is minimum, the path of principle rays depends on the contents of the imaging optical system as shown in FIG. 1(A). For convenience, therefore, there is considered only the diameter $\phi_c|\phi_{min}$ of an on-axis light beams which have passed across the cornea:

$$\phi_c|\phi_{min} = 2D \cdot \tan\theta_1'$$
$$= 2D \cdot \tan M\theta_2'$$

where $\theta_1'$ is equal to $\theta'|\phi_{min}$ and M is a zoom ratio.

If it is desired that the diameter $\phi_c$ of the cornea passing light beams is determined to fulfull the above characteristic (i) under the aforementioned conditions, the zoom ratio M cannot be very increased since the effecting angle $\theta$ is limited in accordance with NA in the fiber. If the zoom ratio M is increased, the imaging optical system L is correspondingly increased in size so that the above characteristic (iv) will also be hard to be attained. For the above reasons, the above prior art coagulator had the zoom ratio M placed in the range of the above characteristic (i). In order to further regulate the spot size, the imaging optical system L may be defocused to cover the regulation range of the characteristic (iii) as shown in FIG. 1(C).

In this system, however, the ejecting end of the fiber is imaged on a position other than the therapeutic region, for example, the retina R (a position P in FIG. 1(C)), so that the energy density in this position P will be higher than that of the therapeutic region. Therefore, the characteristic (ii) cannot be fulfilled. There is also a problem in that any non-therapeutic region may be damaged by coagulating it with the higher energy region of the projected light beams. When the light transmitting members such as the eye lens, vitreous body and the like as well as the iris are therapeutically coagulated, it is very dangerous that the higher energy region of the projected light beams is positioned on the retina or choroid coat. Thus, it may be impossible that the light transmitting member or iris is therapeutically coagulated.

A turret and variable power system, which is another example of the prior art spot size regulating mechanism, will not damage any non-therapeutic region. However, a variable power optical system used therein may be increased in size. For such a reason, a coagulator combined with a slit lamp device cannot help normally reducing the number of steps for regulating the spot size to reduce the variable power optical system in size because there is a problem of a space that the slit lamp is contained. As a result, the range through which the spot size can be regulated will be reduced so that the above characteristic (i) will not be fulfilled as well as the other characteristics (iii) and (iv).

It is an object of the present invention to eliminate the disadvantages in the prior art phototherapeutic apparatus and to provide a new and novel phototherapeutic apparatus which can attain all the above characteristics (i) to (iv).

In order to accomplish the above object, the structural feature of the present invention resides in a phototherapeutic apparatus comprising a source of therapeutic light, a plurality of fiber optical elements having different core diameters, means for selecting the respective one of said fiber optical elements and causing the light beams from said source of therapeutic light to be incident on the selected fiber optical element, and an optical system for projecting the light beams emitted from the selected fiber optical element onto a therapeutic region of a patient's eye. In such an arrangement, the emitting end of the selected fiber optical element provides a secondary source of therapeutic light and also one of the fiber optical elements having different emitting end diameters can freely be selected to regulate the spot size, if desired. This means that the phototherapeutic apparatus can largely be simplified in structure.

The structural feature of the present invention in the more definite embodiment thereof resides in providing the safest phototherapeutic apparatus in therapy and operation, which can provide the highest energy density to a therapeutic region by fulfilling the following relationship for each of the fiber optical elements:

$$2|F \cdot \tan(\sin^{-1}(NA_{Fi}))| > |\beta \cdot \phi_i|$$

where F is the focal length of a projecting optical system for projecting the light beams ejected from the end of the selected fiber optical element; $\beta$ is the magnification of a formed image; $\phi_i$ is the emitting end diameter of the selected fiber optical element; and NA is $NA_{Fi}$.

By causing the emitting end diameters of the fiber optical elements to have the following geometric progression relationship:

$$\phi_{Fi} = M \cdot \phi_{Fi-1} \quad (i=1, 2, 3, \ldots n)$$

and by providing the zoom ratio M of the projecting optical system, the present invention is further advantageous in that the rough regulation of spot size can stepwise be effected in according with the emitting end diameter of the selected fiber optical element and in that the regulation of spot size between each adjacent steps can continuously be carried out by operating the projecting optical system with respect to its zoom magnification. Accordingly, the spot size can continuously be regulated over a very broad range in the whole phototherapeutic apparatus. Moreover, the spot size regulating mechanism including means for selecting one of the fiber optical elements may largely be simplified in construction and also reduced in size.

Figure 2:
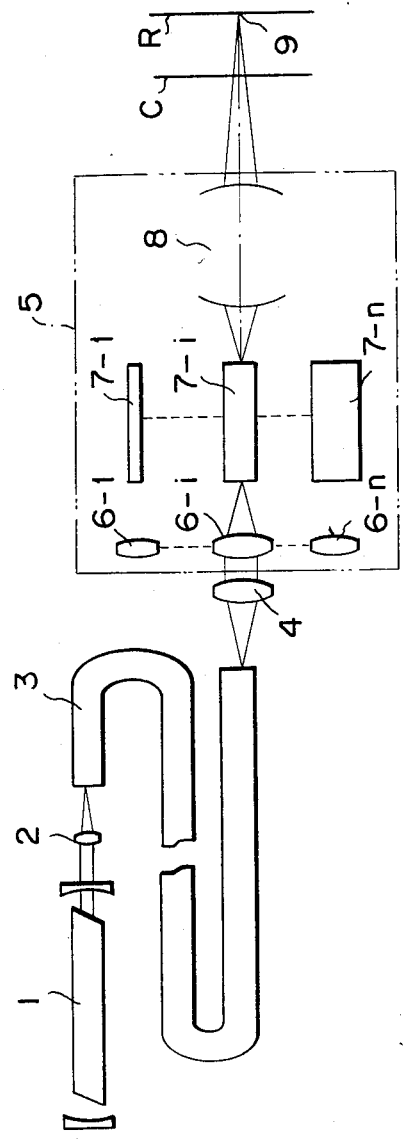
Figure 3:
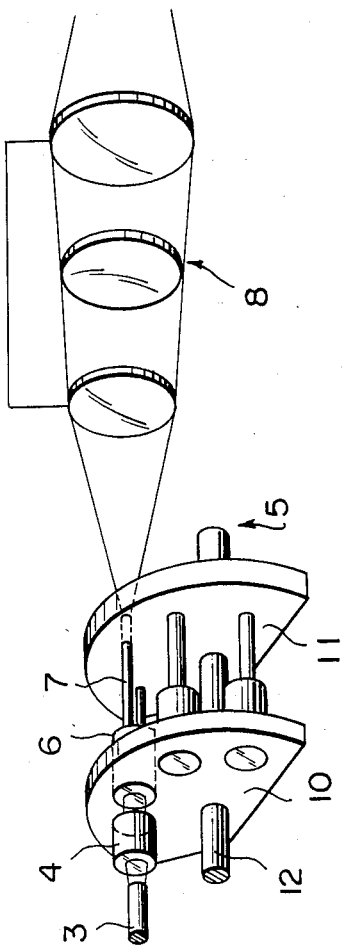

The present invention will now be described by way of example in connection with the drawings. In the drawings:

FIGS. 1(A) to 1(C) are optical diagrams illustrating the principle of a spot size regulating mechanism which is used in the prior art coagulator;

FIG. 2 is an optical diagram of a coagulator according to the present invention; and FIG. 3 is a perspective view of the spot size regulating mechanism shown in FIG. 2.

FIG. 2 is an optical diagram of a coagulator according to the present invention. A laser tube 1 used as a source of therapeutic light emits light beams which are in turn incident on a light conducting optical fiber 3 through a condenser lens 2. Light beams emitted from the optical fiber 3 are converted into parallel beams by a collimator lens 4. The parallel beams are incident on a spot size regulating mechanism 5 which serves also as an optical system for therapeutic laser beams. The spot size regulating mechanism 5 comprises a plurality of condenser lenses 6-1, ... 6-i, ... 6-n one of which can selectively be interposed in the path of the parallel beams from the collimator 4; a plurality of fiber optical elements 7-1, ... 7-i, ... 7-n having different emitting end diameters, each of which has its incident end located at the focus position of the respective one of the condenser lenses 6 and can selectively be interposed in the path of the light beams projected from the corresponding condenser lens 6; and a projecting optical system 8 having a zoom ratio M. FIG. 2 shows such as a state that the condenser lens 6i and fiber optical element 7a are selected and interposed in the path of light beams. In such a state, the emitting end of the selected fiber optical element 7i is imaged through the projecting optical system 8, for example, on a therapeutic region 9 of the retina R with a magnification $\beta$ ($m_o < \beta < M \cdot m_o$ where $m_o$ is the initial magnification and M is the zoom ratio of the projecting optical system 8).

In other words, the near field pattern of the fiber optical element is projected on the therapeutic region. At this time, the spot size $\phi'$ is equal to $\beta \phi_i$ (where $\phi_i$ is the emitting end diameter of the selected fiber optical element: In FIG. 2, it is the emitting end diameter of the fiber optical element 7i). Light beams passing across the cornea C is the far field pattern of the fiber optical element 7i.

If the light beams are incident on any one of the fiber optical elements (its core diameter is $\phi F$, NA is $NA_F =$ - sin θF and the length thereof is L) with a spot diameter of $W_i$ at $NA_i = \sin \theta_i$ ($NA_F \geq NA_i$) the field pattern is substantially levelled. On the other hand, the far field pattern depends on the length L of that fiber optical element and an angular deviation between the optical axis of incident light and the end face of the fiber on which the light beams are incident. If there is no angular deviation since the length L of the fiber is in the order of several tens of centimeters, it is known that the far field pattern widens from $NA_i$ of the incident light beam throughout $NA_F$ of the fiber. The present invention utilizes this inherent characteristic of the fiber optical system to conduct the light beams from a single light source into the fiber optical element $7i$ and then to use the emitting end thereof as a secondary light source so that the spot size can be adjusted by properly selecting the emitting end diameter of the fiber optical element $7i$ and the angle through which the ejected light beams widen.

It has been described hereinbefore that the prior art coagulator has a significant problem in an inconsistency between the importance of an angle through which the ejected light beams widen and the relationship $\beta = 1/\gamma$ between the magnification $\beta$ of an formed image and the angular magnification $\gamma$. The present invention may overcome such a problem.

The zoom projecting optical system 8, which is located rearwardly of the fiber optical element $7i$, is an auxiliary means for covering between each discontinuous changes in the magnitude of the secondary light source, that is, the emitting end diameter of the fiber optical element $7i$. By providing a plurality of fiber optical elements 7, therefore, the zoom ratio M of the zoom projecting optical system can be reduced so that it may be simplified in construction and reduced in size. Considering the operation of the apparatus, the magnitude of the optical system and so on, it is desirable that the number of fiber optical elements is four or more. If the fiber optical elements 7 is sufficient in number and if the discontinuity of spot size associated with the discontinuity of emitting end diameter can be neglected on operation, the projecting optical system 8 is not necessarily a zoom optical system except that it can fulfill the above formula (1). In the illustrated embodiment, the light conducting optical fiber 3 can be replaced by any suitable means which can optically connect the source of laser beam 1 with the spot size regulating mechanism 5. Considering that the source of laser light in the coagulator is increased in size since its power is larger and the spot projecting optical system is normally incorporated into the slit lamp device because of necessity of the increased freedom in the illuminated region, as well as easy operation in the apparatus, the optical fiber 3 is only taken in the illustrated embodiment.

The optical system providing the parallel beams which connects the spot size regulating mechanism 5 with the optical fiber 3 by the use of the collimator lens 4 is effective since it can reduce any output loss due to errors in alignment on manufacturing and spot size changing.

FIG. 3 is a perspective view showing a particular arrangement of the above spot size regulating mechanism according to the present invention. In this arrangement, the collimator lens 4 consists of a known graded index type rod-like lens. Parallel light beams from the collimator lens 4 are received by the respective condenser lens 6 which also consists of a distributed index type rod-like lens. Each of the condenser lens 6 is held in the respective opening which is formed in a circular or fan-shaped plate 10. Each of the fiber optical elements 7 is similarly mounted on a plate 11 at a position faced to the respective condenser lens 6. These two plates 10 and 11 are connected with each other by means of a shaft 12 which is in turn rotatably supported in bearings (not shown). By rotating the shaft 12, any one of the fiber optical elements 7 can be selected.

The invention has thus been shown and described with reference to specific examples, however, it should be noted that the invention is limited only by the appended claims.

I claim:

1. A phototherapeutic apparatus comprising:
   a therapeutic light source for projecting light beams of a selected spot size onto a therapeutic region of a patient;
   spot size regulating means located between said light source and the therapeutic region for regulating the spot size of the light beams projected onto the therapeutic region;
   said regulating means including coarse regulating means for effecting a coarse stepwise change in the spot size and fine regulating means for effecting a fine adjustment in the spot size;
   said coarse regulating means being provided adjacent said light source and including a plurality of illuminating fiber optical elements having different emitting end diameters respectively and means for selecting one of said fiber optical elements so that the light beams from said light source are passed through and emitted from the emitting end of the selected one of the fiber optical elements, whereby said emitting end of said selected fiber optical element functions as a secondary light conduit whose size is determined by the diameter of said emitting end;
   said fine regulating means being located between said coarse regulating means and the therapeutic region and including a variable magnification optical system for projecting and imaging the light beams from said emitting end of the selected one of the fiber optical elements onto the therapeutic region, said magnification optical system having a range of magnification change which is sufficient to substantially cover the differences between emitting end diameters of the fiber optical elements which are adjacent to each other.

2. A phototherapeutic apparatus as defined in claim 1, wherein each of said fiber optical elements fulfills the following relationship:

$$2|F \cdot \tan(\sin^{-1}(NA_{Fi}))| > |\beta \phi_i|$$

wherein F is the focal length of said variable magnification optical system; $\beta$ is the magnification of said variable magnification optical system; $\phi_i$ is the emitting end diameter of said selected optical fiber element; and $NA_{Fi}$ is the numerical aperture of the select4ed optical fiber element.

3. A phototherapeutic apparatus as defined in claim 1, wherein said variable magnification optical system is a zoom lens and said fiber optical elements have a geometric progression relationship relative to one another so that their emitting end diameters can be represented by:

$$\phi_{Fi} = M \cdot \phi_{Fi-1} \text{ (M:constant)}$$

and wherein M is the zoom ratio of said zoom lens.

4. A phototherapeutic apparatus as defined in claim 1, wherein the light beams from said source of therapeutic light are incident on said selected fiber optical element through an optical fiber.

5. A phototherapeutic apparatus as defined in claim 1, further comprising a collimator lens located between said source of therapeutic light and said fiber optical elements for converting the light beams from said source of therapeutic light into parallel beams and condenser lenses each disposed relative to the respective one of said fiber optical elements between said source of therapeutic light and that fiber optical element for condensing said parallel beams from said collimator lens onto the incident end of the fiber optical element.

6. A phototherapeutic apparatus as defined in claim 5 wherein said collimator lens and/or condenser lenses are in the form of a distributed index rod lens.

7. A phototherapeutic apparatus in accordance with claim 1 in which said therapeutic light source is a laser source.

* * * * *